(12) United States Patent
Nagatomi et al.

(10) Patent No.: US 9,283,298 B2
(45) Date of Patent: Mar. 15, 2016

(54) COMPLIANT SURGICAL ADHESIVE

(71) Applicant: Clemson University, Clemson, SC (US)

(72) Inventors: Jiro Nagatomi, Seneca, SC (US); C. Kenneth Webb, Clemson, SC (US); Olin Thompson Mefford, Clemson, SC (US); Lindsey Sanders, Seneca, SC (US); Roland Stone, Charleston, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 14/495,103

(22) Filed: Sep. 24, 2014

(65) Prior Publication Data

US 2015/0086503 A1    Mar. 26, 2015

Related U.S. Application Data

(60) Provisional application No. 61/882,138, filed on Sep. 25, 2013.

(51) Int. Cl.
*A61L 24/06* (2006.01)
*A61L 24/00* (2006.01)
*A61L 24/04* (2006.01)

(52) U.S. Cl.
CPC ............ *A61L 24/001* (2013.01); *A61L 24/0031* (2013.01); *A61L 24/043* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 8,461,316 B1 | 6/2013 | Sung et al. | |
| 8,492,501 B2 | 7/2013 | Bell et al. | |
| 8,501,232 B2 | 8/2013 | Talton et al. | |
| 8,518,450 B2 | 8/2013 | Kalombo | |
| 2009/0098083 A1* | 4/2009 | Hubbell | A61K 47/48215 424/78.27 |

* cited by examiner

*Primary Examiner* — Jeffrey Mullis
(74) *Attorney, Agent, or Firm* — Dority & Manning, P.A.

(57) ABSTRACT

Surgical adhesives that include a blend of two different thermoreversible gelling polymers and a crosslinking agent are described. The first thermoreversible gelling polymer is partially or fully acrylated and the second thermoreversible gelling polymer includes dual functionality including acrylate functionality and amine-reactive functionality. The adhesives can provide gelling and covalent crosslinking within the polymers of the adhesive as well as crosslinking with surrounding tissue.

22 Claims, 2 Drawing Sheets

COMPLIANT SURGICAL ADHESIVE

STATEMENT REGARDING FEDERALLY SPONSORED RESEARCH OR DEVELOPMENT

This invention was made with government support under Grant/Contract No. R21EB008785 awarded by the National Institutes of Health. The government has certain rights in the invention.

BACKGROUND

Biocompatible adhesives have potential for use in a large variety of medical applications including as hemostats, sealants, glues, and so forth. Surgical applications for adhesives show particular promise. For example, approximately 600,000 hysterectomies are performed annually in the United States, and one of the most common complications during hysterectomy surgeries is accidental laceration to the bladder. Current treatment for such bladder injuries is limited to sutures, which prevents proper distention of the bladder wall during filling and necessitates use of a catheter during recovery.

Surgical adhesives require bulk strength and pliability to maintain unitary construction and avoid rips and tears and also require adhesive strength to avoid leakage at the application site. Attaining a useful balance in both qualities has proven difficult, particularly when considering applications involving highly expandable tissue, such as bladder and lung applications. Although a number of tissue adhesives and sealants approved by the FDA for surgical use are currently available, none of them are suitable for application to the bladder because of inadequate strength, compliance, or biocompatibility issues.

What is needed in the art is a surgical adhesive that can exhibit high bulk strength, compliability, and high adhesive qualities.

SUMMARY

According to one embodiment, disclosed is a surgical adhesive that includes a blend of two different polymers. The first polymer is a thermoreversible gelling block copolymer that includes a hydrophilic block and a hydrophobic block. The first polymer also includes reactive functionality (such as acrylate, maleimide or vinyl sulfone) on at least a portion of the termini of the polymer suitable for covalent crosslinking via Michael-type addition with a multi-functional thiol compound. The second polymer of the blend is also a thermoreversible gelling polymer and includes a hydrophilic block and a hydrophobic block. The second polymer includes reactive functional groups on a portion of the termini suitable for crosslinking via Michael-type addition and also includes amine-reactive functionality on a portion of the termini suitable for covalent reaction with proteins present in tissue. The hydrophilic blocks and hydrophobic blocks of the two polymers can be the same or different, but the two polymers will differ in some manner, e.g., with regard to functional groups on the polymers. The blend will include the two polymers in a ratio of from about 10:90 to about 90:10 by weight of the first and second polymers, respectively. The surgical adhesive also includes a polyfunctional thiol crosslinker.

Also disclosed is an adhesive system for use in biological applications. The adhesive system includes the surgical adhesive and also includes the polyfunctional thiol crosslinker that is held separately from the surgical adhesive prior to use. During use, the two components of the system can be applied to a biological site upon which the thermoreversible polymers can gel at the local temperature (e.g., body temperature), and the polyfunctional thiol crosslinker can crosslink the polymers of the adhesive via the acrylate functionality of the polymers. The amine-reactive functionality of the second polymer can crosslink the polymers with tissue at the application site, thus forming a strong, pliable and highly adhesive seal at the site of use.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which.

DETAILED DESCRIPTION

Figure 1:
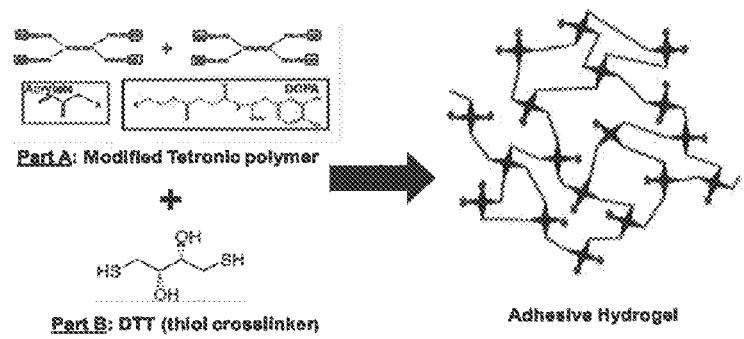
FIG. 1 schematically illustrates one method of forming the surgical adhesive as described herein.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment may be used in another embodiment to yield a still further embodiment. Thus, it is intended that the present disclosure cover such modifications and variations as come within the scope of the appended claims and their equivalents.

The present disclosure is generally directed to surgical adhesives. More specifically, the surgical adhesives include a blend of two different thermoreversible gelling polymers. The adhesives can provide excellent bulk strength, pliability, and tissue adhesive qualities. The surgical adhesives can be beneficially utilized in a wide variety of medical applications such as surgical applications, for hemostasis, in reconstruction, and so forth. In one embodiment, the surgical adhesive can be utilized in surgical applications involving highly expandable organs such as the bladder or lungs.

The thermoreversible polymers of the biological adhesive are biocompatible block copolymers that include a hydrophilic block and a hydrophobic block. The block copolymers are selected to exhibit thermoreversible sol-gel behavior, existing as a low viscosity solution at room temperature and transitioning to a viscoelastic gel at physiological temperature. As utilized herein, a block of the copolymers refers to a portion of the polymer that includes multiple contiguous monomeric units (e.g., greater that about 10 contiguous monomeric units). The relative proportions of the two blocks can be such that at the physiological conditions of use (e.g., from about 30° C. to about 45° C.), the hydrophobic blocks of the polymers will associate, leading to gelation of the polymers and formation of a cohesive hydrogel at the application site. For example, from about 10% to about 50% of the thermoreversible block copolymers can be formed of hydrophobic blocks.

While either or both of the hydrophilic blocks and the hydrophobic blocks of the thermoreversible block copolymers of the blend can be the same, this is not a requirement of the blend. For example, both blocks of all copolymers of the blend can be identical, and the different block copolymers can vary in only the functionality of the block copolymers. In other embodiments, one or more blocks of the copolymers of the blend can differ as to, e.g., block structure, block size, proportions of hydrophobic to hydrophilic blocks, etc.

In one embodiment, one or more of the block copolymers of the blend can be a linear block copolymer of the formula A-B-A. Block copolymers commonly referred to as poloxamers are suitable for use in forming the thermoreversible gelling copolymers. Poloxamers are block copolymers of polyethylene oxide (PEO) and polypropylene oxide (PPO). The general structure for poloxamers is the PEO-PPO-PEO structure of $HO(CH_2CH_2O)_a(CH(CH_3)CH_2O)_b(CH_2CH_2O)_cH$ where b is at least 15 and $(CH_2CH_2O)$ a+c is varied from about 20% to about 90% by weight. The polypropylene oxide segment is hydrophobic; the polyethylene oxide segment is hydrophilic. Aqueous polymeric solutions of poloxamers undergo microphase transitions at a lower/upper critical solution temperature, causing a characteristic gel formation. This transition is dependent on concentration and composition of the block copolymer.

Other copolymers that include polyethylene oxide blocks and polypropylene oxide blocks can be use in addition to poloxamer cores in forming the thermoreversible gelling copolymers. For instance meroxapols PPO-PEO-PPO copolymers may be used.

Other polymer blocks that may be included in the thermoreversible block copolymer include hydrophilic blocks such as polyvinyl alcohol, polyvinyl-pyrrolidone, polyacrylic acids, esters and amides, soluble celluloses, peptides and proteins (e.g., albumin, fibronectin, laminin, elastin, fibrinogen), vitronectin, dextrans, gelatin, chitosan, heparin, chondroitin sulfate, keratan sulfate, dermatan sulfate, alginate, hyaluronic acid, and other polysaccharides. Additionally, polymer blocks with an upper critical point may be used, such as other polyalkylene oxides, such as mixed polyalkylene oxides and esters, derivatized celluloses, such as hydroxypropylmethyl cellulose, and natural gums such as konjac glucomannan.

Polyethylene glycol (PEG) hydrophilic blocks can be combined with a variety of different hydrophobic blocks to form a copolymer backbone. For instance, block copolymers of PEG with blocks formed of lactide, glycolide, caprolactone, and so forth to form the thermoreversible gelling copolymers. For instance, PEG can be combined with poly(lactide-co-glycolide) (PLGA) to form tri-block copolymers of either the BAB orientation or the ABA orientation for use in forming the thermoreversible gelling copolymers. Similarly, PEG blocks and poly(lactic-co-ε-caprolactone) can be utilized.

The thermoreversible gelling block copolymers are not limited to linear polymers and can include multiple arms. Multi-armed polymers suitable for use include multi-arm-polyethylene glycols such as 3-arm-polyethylene glycol (3 armPEG), 4-arm-polyethyleneglycol (4 armPEG), 6-arm-polyethyleneglycol (6 armPEG) and 8-arm-polyethyleneglycol (8 armPEG). In one embodiment, multi-armed PPO/PEO block copolymers can be utilized such as the Tetronic® series (4 arm-PPO-PEO). The 4 arm-PPO-PEO block copolymers are tetra-functional poloxamines having the general structure of:

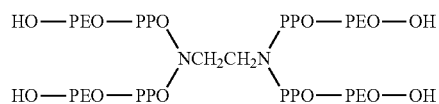

These hydroxyl functionalized multi-armed block copolymers can be useful in forming the thermoreversible gelling polymers of the surgical adhesive due to the multiple hydroxyl functionality of the polymers, which can provide routes to formation of the desired functionalities of the thermoreversible gelling polymers, the biocompatibility of the polymers, and the multiple arms, which can provide increased density of the functionality of the thermoreversible gelling polymers.

Other block copolymers as can be utilized in forming the thermoreversible gelling copolymers include polyetherester copolymers such as PEG (polyethylene glycol)/PBT polylbutylene terephthalate) copolymers. Such copolymers are available from IsoTis, Inc. of the Netherlands and are described in U.S. Pat. No. 5,980,948 issued on Nov. 9, 1999 to Goedemoed et al., the entire contents of which are hereby incorporated by reference. Such polymers are available as Polyactive™.

The block copolymers can include functionality that can be manipulated to form the thermoreversible gelling copolymers of the blend that forms the surgical adhesive. More specifically, the block copolymers can be manipulated to include crosslinkable groups, e.g., acrylate, maleimide, or vinyl sulfone reactive functionality that permit the thermoreversible gel to be covalently crosslinked via a polyfunctional crosslinking agent at the application site, e.g., a polyfunctional thiol crosslinking agent. After crosslinking, the gels are irreversibly crosslinked; however, they retain other significant thermoresponsive properties, such as changes in volume and in permeability. The blend of thermoreversible gelling block copolymers can include at least two thermoreversible gelling block copolymers.

A first thermoreversible gelling copolymer of the blend can be either partially or fully acrylated. The methodology used to form the full or partial acrylation of the first copolymer is not particularly limited, and preferred routes can depend upon the initial functionality of the block copolymer utilized. For instance, when utilizing a hydroxyl-terminated block copolymer, the block copolymer can be fully or partially acrylated via reaction with acryloyl chloride in the presence of trimethylamine according to standard chemistry.

The first block copolymer can generally be about 50% or more acrylated at the termini of the block copolymer. For instance, when partially acrylated, the block copolymer can be from about 50% to about 95% acrylated, or from about 60% to about 90% acrylated.

When partially acrylated, in one embodiment the remaining termini of the first block copolymer can carry biologically active agents, such as detectable labels (e.g., fluorescent or phosphorescent labels and the like), hemostatic agents or other drugs for delivery to the targeted site, and so forth. In one embodiment, the remaining termini of the first block copolymer can carry a delivery vehicle, such as a nanoparticle, that can in turn carry a biologically active agent for delivery at the targeted site. A biologically active agent can be released from the delivery vehicle over the course of time at the targeted site, for instance via degradation of the delivery vehicle. By way of example, representative drug delivery systems can include, without limitation, nanoparticle delivery vehicles as described in U.S. Pat. No. 8,518,450 to Kalombo, U.S. Pat. No. 8,501,232 to Talton, et al., U.S. Pat. No. 8,492,501 to Harth, et al., and U.S. Pat. No. 8,461,316 to Sung, et al., all of which are incorporated herein by reference.

A second thermoreversible gelling block copolymer of the blend can be dual functionalized to include crosslinking functionality on a portion of the copolymer termini and to also include amine-reactive functionality on another portion of the copolymer termini. The amine-reactive functionality of the second block copolymer can form crosslinks with primary amine groups of tissue at the targeted site and can form a strong adhesive bond between the surgical adhesive gel and the tissue.

Any biocompatible amine-reactive functionality can be utilized on the second block copolymer including, without limitation, aldehyde, carbodiimide, sulfonyl chloride, isothiocyanate, isocyanate, acyl azide, anhydride, fluorobenzene, carbonate, N-hydroxysuccinimide ester, imidoester, epoxide, fluorophenyl ester, phenol derivatives, aniline derivatives, and combinations thereof. Phenol derivatives as may be utilized in the block copolymer can include, without limitation, tyramine, hydroxyphenylacetic acid, derivatives thereof, and a combination thereof. Aniline derivatives can include, without limitation, hydroxyethylaniline, aminoethylaniline, aminobenzyl alcohol, derivatives thereof, and/or combinations thereof.

In one embodiment, the amine-reactive functionality of the second block copolymer can include a dihydroxyphenyl derivative. Dihydroxy phenol derivatives have become of interest in the development of medical adhesives. One particular dihydroxyphenyl derivative is L-3-4-dihydroxyphylalanine (L-DOPA); an amino acid that is believed to be responsible for the adhesion of mussels to a variety of different surface types. The dihydroxy phenol derivative can include, without limitation, L-DOPA, dopamine, 3,4-dihydroxyphenyl ethanol, 3,4-dihydroxyhydrocinnamic acid, norepinephrine, epinephrine, derivatives thereof, and/or combinations thereof.

The second block copolymer can be functionalized with the amine-reactive functionality according to standard chemistry. For instance, in one embodiment, a block copolymer can first be partially acrylated and following, the remaining termini of the block copolymer can be functionalized with a succinimide group followed by reaction with L-DOPA to form the second block copolymer.

The second block copolymer can generally include the acrylate functionality and the amine-reactive functionality in a ratio of from about 1:3 to about 3:1, for instance from about 2:1 to about 1:2, respectively.

The surgical adhesive can include the first and second thermoreversible gelling block copolymers in a blend. In general the blend can include the two polymers in a ratio of the first block copolymer (i.e., the partially or fully acrylated block copolymer) to the second block copolymer (i.e., the dual functional block copolymer including acrylate functionality and amine-reactive functionality) of from about 10:90 to about 90:10, for instance from about 40:60 to about 85:15, or from about 50:50 to about 80:20. In one embodiment, the blend can include a ratio of the first block copolymer to the second block copolymer of about 75:25.

A composition including the blend of thermoreversible gelling polymers can be applied to a surface to be treated. For example, the blend of block copolymers can be formulated in conjunction with a pharmaceutically acceptable carrier as is generally known in the art. A pharmaceutically-acceptable carrier can encompass any material, composition or vehicle, such as a liquid or solid filler, diluent, excipient, solvent or encapsulating material that can be combined with the blend of thermoreversible gelling polymers. A pharmaceutically-acceptable carrier should be compatible with the other ingredients of the composition and not injurious to the targeted tissue or subject. Examples of materials that may serve as pharmaceutically-acceptable carriers include, without limitation, sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; phosphate buffered saline with a neutral pH and other non-toxic compatible substances employed in pharmaceutical formulations.

In one embodiment, the blend of thermoreversible gelling block copolymers can be applied as a "patch" that includes any shaped substrate compatible with surgical implantation and capable of being coated by the surgical adhesive. The surgical adhesive can be formulated for use as an aqueous suspension, a solution, a powder, a paste, a sheet, a ring, a stent, a cone, a plug, a pin, a screw and complex three-dimensional shapes contoured to be complementary to specific anatomical features. Substrate materials can include, without limitation, collagen; polylactic acid; hyaluronic acid; fluoropolymers; silicones; knitted or woven meshes of, for example, cellulosic fibers, polyamides, rayon acetates and titanium; skin; bone; titanium and stainless steel. Alternatively, pericardial or other body tissue may be used as a substrate for the surgical adhesive. In general the substrate can be flexible, such as a fibrous sheet readily formed into a variety of shapes that is bioabsorbable. A flexible patch can serve to enhance sealant strength while allowing some penetration of the surgical adhesive thereto. Optionally, in a surgical setting, a dry or a wetted absorbent gauze can be placed proximal to a wound site in order to wick away any excess of the blend of copolymers prior to cure.

A composition including the blend of thermoreversible gelling polymers can be delivered in conjunction with a propellant that is provided in fluid communication with a spray nozzle tip. Propellants include aerosol propellants such as carbon dioxide, nitrogen, propane, fluorocarbons, dimethyl ether, hydrochlorofluorocarbon-22,1-chloro-1,1-difluoroethane, 1,1-difluoroethane, and 1,1,1-trifluoro-2-fluoroethane, alone or in combination.

During use, a composition including the blend of the first and second polymers can be applied to a site in conjunction with a polyfunctional thiol crosslinker that can crosslink the polymers via the acrylate functionality. The polyfunctional thiol crosslinker can be held separately from the blend of the copolymers prior to application at a targeted site. Immediately prior to or during application of the blend to the tissue, the polyfunctional thiol crosslinked can be combined with the composition including the blend of block copolymers such that the thermoreversible gel can be covalently crosslinked upon application at the site. For example, a multi-lumen syringe or other application device can be utilized that can deliver the two components of the adhesive system concurrently at the targeted site. Alternatively, the two components can be mixed and applied at the targeted site together immediately following mixing. When considering the utilization of the surgical adhesive in conjunction with a patch, the polyfunctional thiol crosslinker can be applied to the patch immediately prior to application at the site and following or concurrently with the application of the blend of thermoreversible gelling block copolymers to the site.

In general, the polyfunctional thiol crosslinker can be any polythiol having two or more —SH groups. Examples of suitable polyfunctional thiol crosslinked include, but are not limited to, the esters of thioglycolic acid, 2-mercapto-propionic acid or 3-mercaptopropionic acid with polyols, such as glycols, pentaerythritol, di-pentaerythritol and trimethylolpropane, and optionally a fatty acid, such as oleic acid, stearic acid, isononanoic acid or sunflower fatty acid. Specific examples of suitable thiol compounds are dithiothreitol, ethylene glycol bis(thioglycolate), ethylene glycol bis(2-mercaptopropionate), ethylene glycol bis(3-mercaptopropionate), pentaerythritol tetrakis(thioglycolate), pentaerythritol tetrakis(2-mercaptopropionate), pentaerythritol tetrakis(3-mercaptopropionate), trimethylolpropane tris(2-mercaptopropionate), trimethylolpropane tris(3-mercaptopropionate), and the condensation product of di-trimethylolpropane, 2,2-dimethylolpropionic acid, stearic acid, and 3-mercaptopropionic acid.

The polyfunctional thiol crosslinker can be monomeric or polymeric, as desired. For instance, a polymeric thiol crosslinker can be utilized in one embodiment to affect characteristics (e.g., pliability) of the crosslinked adhesive. By way of example, in one embodiment, the thiol crosslinker can have a general structure of:

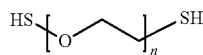

in which n is greater than 1.

The surgical adhesive can be administered in vivo, for example, to a human, or to an animal, or parenterally such as by injection, implantation (e.g., subcutaneously, intracranially, or intradermally), administration to mucosal membranes (e.g., intranasally, intravaginally, intrapulmonary, buccally), or in situ delivery (e.g., by aerosol spray) to apply the surgical adhesive to the targeted site. The adhesives can be utilized for wound closure, such as a dura sealant. In one particular embodiment, the surgical adhesives can be utilized on wound repair with highly expandable tissue, e.g., bladder or lung tissue.

As used herein, a wound includes damage to any tissue in a living organism. The tissue may be an internal tissue, such as the stomach lining, dura mater or pachymeninx or a bone, or an external tissue, such as the skin. As such a wound may include, but is not limited to, a gastrointestinal tract ulcer, a broken bone, a neoplasia, or cut or abraided skin. A wound may be in a soft tissue, such as the spleen, or in a hard tissue, such as bone. The wound may have been caused by any agent, including traumatic injury, infection or surgical intervention. As such, the surgical adhesives can be "tissue sealants," which are substances or compositions that, upon application to a wound, seals the wound, thereby reducing blood loss and maintaining hemostasis.

FIG. 1 illustrates one method of forming and utilizing the surgical adhesive. In this embodiment, the blend can include two thermoreversible gelling polymers that are both based upon a 4 arm-PPO-PEO block poloxamines. The first copolymer of the blend can be fully acrylated. The second copolymer can be partially acrylated and can include DOPA functionality as the amine-reactive functionality of the second copolymer. Upon interaction with the thiol crosslinker, the two polymers can form covalent crosslinks with each other to form the adhesive hydrogel, and the amine-reactive functionality can be maintained so as to form crosslinks with amine groups of the tissue to which the adhesive is applied.

The present disclosure may be further understood with reference to the examples, below.

Example 1

A bi-functional thermoreversible gelling copolymer was prepared through multi-step process. Acrylation was first performed on a PEO/PPO block copolymer (Tectronic® T1107, MW=15,000) in dicholormethane. Briefly, Tetronic® T1107 with triethlyamine (TEA) and acryloyl chloride was stirred for 24 hours. Triethlyammonium precipitate was filtered out and the product was neutralized to pH 7.0, and then washed with ethyl ether. A partially acrylated T1107 copolymer was then modified using click chemistry to replace the unreacted terminal hydroxyl groups with N-hydroxysuccinimide (NHS) through two reactions (1) 4-dimethylaminopyridine (DMAP) and Succinic Anhyride in tetrahydrofuran (THF) for 12 hours, and (2) NHS and dicyclohexylcarbodimide (DCC) in THF for 4 hours. Acrylation percent and NHS conversion rate for the bi-functional copolymer (NHS+) were 63% and 25%, respectively with 57% product yield.

A fully acrylated block copolymer was used to form a blend with the bi-functional copolymer. Acrylation percent and product yield for the fully acrylated copolymer T1107-acrylate (NHS−) were 93% and 63%, respectively. Four blend ratios (100:0, 75:25, 50:50, 25:75) of the fully acrylated copolymer (NHS−) and the bi-functional copolymer (NHS+) were prepared at a final macromer concentration of 30% w/v with pH adjusted to 7.4.

Chemical crosslinking of acrylate-ends was achieved by addition reaction with appropriate amount of thiol-group donor, dithiothreitol (DTT).

Figure 2:
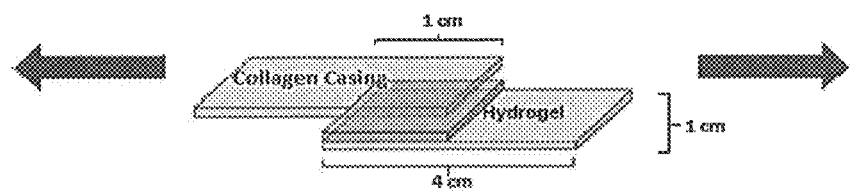
FIG. 2 illustrates an experimental design for testing the bond strength of the surgical adhesive.

Bonding strength of modified T1107 hydrogels as tissue adhesives was investigated using ASTM F2255-05. The experimental design is illustrated in FIG. 2. Dehydrated collagen tissues (DeWied International Inc., TX) were reconstructed for 1 h in 1×PBS then glued onto aluminum fixtures using cyanoacrylate adhesive (Adhezion Biomedical, PA) and cured at room temperature for 24 h. The tissue samples were cut to size (4 cm×1 cm) strips and rehydrated in 37° C. water bath for 1 h. Hydrogel aliquots were mixed as described above to apply 50 µL of adhesive on the tissue surface. Another tissue strip was placed on top to obtain a 1 cm×1 cm applied adhesive area. The bonded tissue samples were allowed to cure for 1 h, wrapped in PBS soaked gauze at 37° C. All samples were subjected to uniaxial strain until failure in lap shear at constant crosshead speed of 10 mm min-1 on MTS Synergie 100 (Eden Prairie, Minn.). The adhesive bonding strength was calculated by maximum load divided by bonded area. Data were plotted as bond strengths (kPa) and statistically analyzed using ANOVA and Tukey's HSD post-hoc testing for comparison of different blend ratios.

Figure 3:
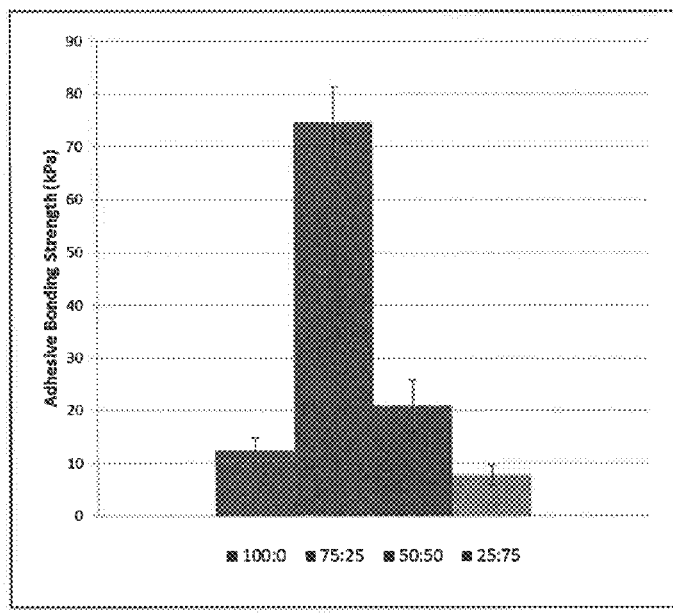
FIG. 3 graphically illustrates the bond strength of several adhesive formulations as described herein.

The strength of the blended hydrogels to adhere hydrated biological surfaces together vastly increases with incorporation of the bi-functional copolymer (NHS+). Further, the 75:25 blend shows a six-fold increase in bonding strength over the sample with no NHS (100:0) (FIG. 3). Also to note, each blend contained different modes of failure. The 100:0 and 75:25 showed adhesive failure, when the rest of the blends failed cohesively.

Example 2

Adhesives were prepared from blends (100:0, 75:25) of fully acrylated T1107 (NHS−) and bi-functional T1107 (NHS+) and crosslinked with DTT, as described in Example 1.

Figure 4:
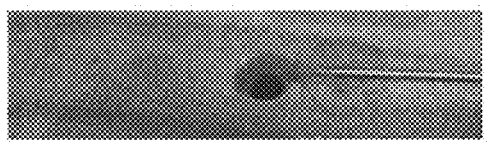
FIG. 4 illustrates an experimental design for testing the burst pressure of a bladder.

Maximum pressures held by punctured rat bladders (Pel-Freez Biologicals Inc., AR) sealed with modified T1107 adhesive were evaluated using a custom ex vivo device as illustrated in FIG. 4. Bladders were stored in 30% sucrose solution at 4° C. until testing. Prior to testing, a small, approximately 2 mm puncture was made on the dome of the bladder using an 18 gage needle. The bladder was sutured and super glued to a shaved 18 gage needle to eliminate leakage from attachment site during testing, then warmed to 37° C. A 50 µl adhesive sample of modified T1107/DTT (200 µl to 25 µl ratio, pH=7.4) was applied to the hole and allowed to cure for 1 h in 37° C. hydrated condition. Testing was performed on a submersed bladder within warmed (37° C.) saline solution. The specimen was subjected to increasing intravesicular pressure using a Harvard Apparatus 11 Plus Pump (Harvard Apparatus, MA) and a 60 ml syringe at a flow rate of 0.8 ml/min until failure, which was evidenced by saline solution colored with calcein blue dye, indicating leakage. Pressures were measured and recorded using LabView software then exported to analyze. A whole, unpunctured bladder was used as a control for testing.

Figure 5:
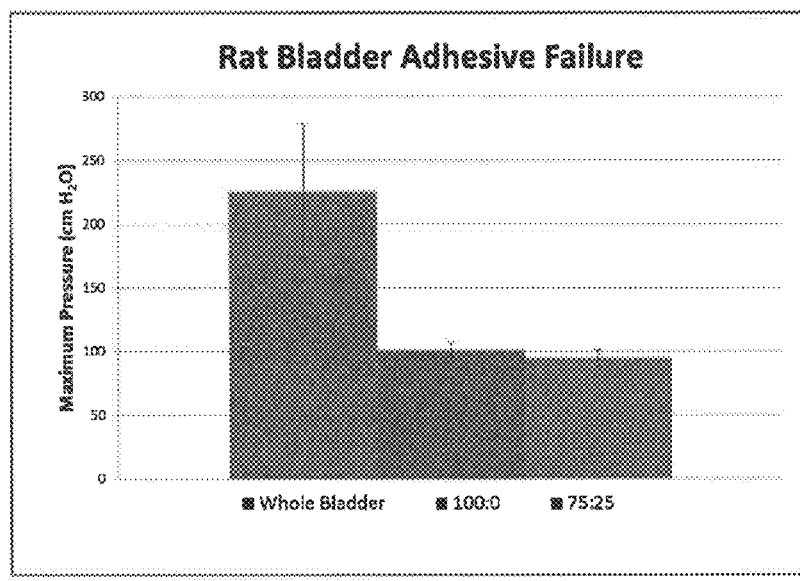
FIG. 5 graphically illustrates the maximum burst pressures for punctured bladders following repair with adhesive formulations as described herein.
Figure 6:
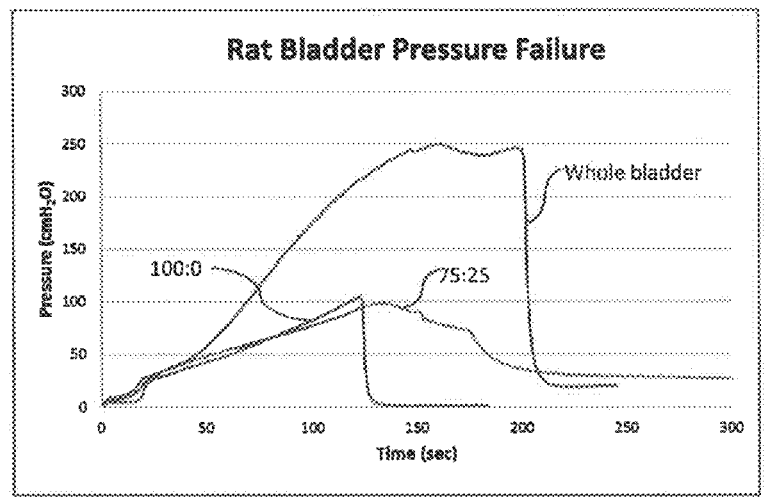
FIG. 6 graphically illustrates the pressure vs. time trends of the bladders of FIG. 2 during testing.

Both blends, 100:0 and 75:25 (NHS−:NHS+), were able to hold physiological pressures needed for bladder application in burst pressure testing. There was no significant difference between the blends (FIG. 5). Further, the pressure trends of the bladders with adhesive sealing the puncture resembled the trend of the non-punctured bladder control, which shows promising results for the bi-functional adhesive's pliability quality (FIG. 6).

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A gel-forming composition comprising:
   a first thermoreversible gelling block copolymer that includes a hydrophilic block and a hydrophobic block, the first thermoreversible gelling copolymer including acrylate functionality in at least a portion of the termini of the copolymer;
   a second thermoreversible gelling block copolymer that differs from the first thermoreversible gelling block copolymer and includes a hydrophilic block and a hydrophobic block, the second thermoreversible gelling copolymer including acrylate functionality on a portion of the termini of the copolymer and further including amine-reactive functionality on a portion of the termini, the hydrophilic block of the second thermoreversible gelling block copolymer being the same or different as the hydrophilic block of the first thermoreversible gelling block copolymer and the hydrophobic block of the second thermo reversible gelling block copolymer being the same or different as the hydrophobic block of the first thermoreversible gelling block copolymer; and
   a polyfunctional thiol crosslinker;
   the composition comprising the first thermoreversible gelling block copolymer and the second thermoreversible gelling block copolymer in a blend at a ratio of from about 10:90 to about 90:10 by weight, respectively.

2. The composition of claim 1, wherein the first and/or the second thermoreversible gelling block copolymer includes a polyethylene oxide as the hydrophilic block.

3. The composition of claim 1, wherein the first and/or the second thermoreversible gelling block copolymer includes a polypropylene oxide as the hydrophobic block.

4. The composition of claim 1, wherein the first and second thermoreversible gelling copolymers each independently include between about 10% and about 50% of the hydrophobic block.

5. The composition of claim 1, wherein at least one of the first and second thermoreversible gelling copolymers is a linear polymer.

6. The composition of claim 1, wherein at least one of the first and second thermoreversible gelling copolymers is a multi-armed polymer.

7. The composition of claim 1, wherein at least one of the thermoreversible gelling copolymers is a 4 arm-polypropylene oxide-polyethylene oxide block copolymer.

8. The composition of claim 1, wherein at both of the thermoreversible gelling copolymers include a 4 arm-polypropylene oxide-polyethylene oxide block copolymer.

9. The composition of claim 8, wherein the 4 arm-polypropylene oxide-polyethylene oxide block copolymer is a tetra functional poloxamine.

10. The composition of claim 1, wherein the first thermoreversible gelling block copolymer is fully acrylated.

11. The composition of claim 1, wherein the first thermoreversible gelling block copolymer is partially acrylated.

12. The composition of claim 11, wherein the first thermoreversible gelling block copolymer is from about 50% to about 95% acrylated.

13. The composition of claim 11, wherein the partially acrylated copolymer comprising remaining termini, the remaining termini carrying one or more biologically active agents.

14. The composition of claim 1, the amine-reactive functionality of the second thermoreversible gelling block copolymer comprising functionality selected from the group consisting of aldehyde, carbodiimide, sulfonyl chloride, isothiocyanate, isocyanate, acyl azide, anhydride, fluorobenzene, carbonate, N-hydroxysuccinimide ester, imidoester, epoxide, fluorophenyl ester, phenol derivatives, aniline derivatives, and combinations thereof.

15. The composition of claim 1, the amine-reactive functionality of the second thermoreversible gelling block copolymer comprising a dihydroxyphenyl derivative.

16. The composition of claim 15, the dihydroxyphenyl derivative comprising L-3-4-dihydroxyphenylalanine, dopamine, 3,4-dihydroxyphenyl ethanol, 3,4-dihydroxyhydrocinnamic acid, norepinephrine, epinephrine, derivatives thereof, and/or combinations thereof.

17. The composition of claim 1, the second thermoreversible gelling block copolymer comprising the acrylate functionality and the amine-reactive functionality in a ratio of from about 1:3 to about 3:1.

18. The composition of claim 1, comprising the first thermoreversible gelling block copolymer and the second thermoreversible gelling block copolymer in the blend at a ratio of from about 50:50 to about 80:20 by weight.

19. The composition of claim 1, further comprising a pharmaceutically acceptable carrier.

20. The composition of claim 1, wherein the polyfunctional thiol crosslinker is monomeric.

21. The composition of claim 1, wherein the polyfunctional thiol crosslinker is polymeric.

22. An application device containing the composition of claim 1 in the form of a surgical adhesive, comprising the blend of the first and second thermoreversible gelling block copolymers and the polyfunctional thiol crosslinker held separately from the blend of the first and second thermoreversible gelling block copolymers.

* * * * *